United States Patent
Siegert et al.

(10) Patent No.: US 8,450,507 B2
(45) Date of Patent: May 28, 2013

(54) INTEGRATED METHOD FOR THE PREPARATION OF TRIOXANE FROM FORMALDEHYDE

(75) Inventors: Markus Siegert, Heidelberg (DE); Neven Lang, Mannheim (DE); Eckhard Stroefer, Mannheim (DE); Christoph Sigwart, Weinheim (DE)

(73) Assignee: BASF SE (DE)

( * ) Notice: Subject to any disclaimer, the term of this patent is extended or adjusted under 35 U.S.C. 154(b) by 891 days.

(21) Appl. No.: 12/304,223

(22) PCT Filed: Jun. 11, 2007

(86) PCT No.: PCT/EP2007/055694
§ 371 (c)(1),
(2), (4) Date: Dec. 10, 2008

(87) PCT Pub. No.: WO2007/144320
PCT Pub. Date: Dec. 21, 2007

(65) Prior Publication Data
US 2009/0187033 A1    Jul. 23, 2009

(30) Foreign Application Priority Data

Jun. 12, 2006   (EP) .................................. 06115287

(51) Int. Cl.
*C07D 323/06* (2006.01)

(52) U.S. Cl.
USPC ......................................................... 549/368

(58) Field of Classification Search
USPC ......................................................... 549/368
See application file for complete search history.

(56) References Cited

U.S. PATENT DOCUMENTS

| | | | |
|---|---|---|---|
| 5,766,424 A * | 6/1998 | Arnold et al. | ................... 203/74 |
| 6,200,429 B1 | 3/2001 | Freyhof et al. | |
| 2007/0155972 A1 | 7/2007 | Lang et al. | |

FOREIGN PATENT DOCUMENTS

| | | |
|---|---|---|
| CA | 2549897 A1 | 7/2005 |
| CA | 2617479 A1 | 2/2007 |
| CA | 2623573 A1 | 2/2007 |
| WO | WO-2005/063353 A1 | 7/2005 |
| WO | WO-2005/063733 A1 | 7/2005 |
| WO | WO-2007/017410 A1 | 2/2007 |
| WO | WO-2007/017479 A1 | 2/2007 |

* cited by examiner

*Primary Examiner* — Andrew D Kosar
*Assistant Examiner* — Raymond Covington
(74) *Attorney, Agent, or Firm* — Novak Druce Connolly Bove + Quigg LLP

(57) ABSTRACT

An integrated process for preparing trioxane from formaldehyde.

13 Claims, 1 Drawing Sheet

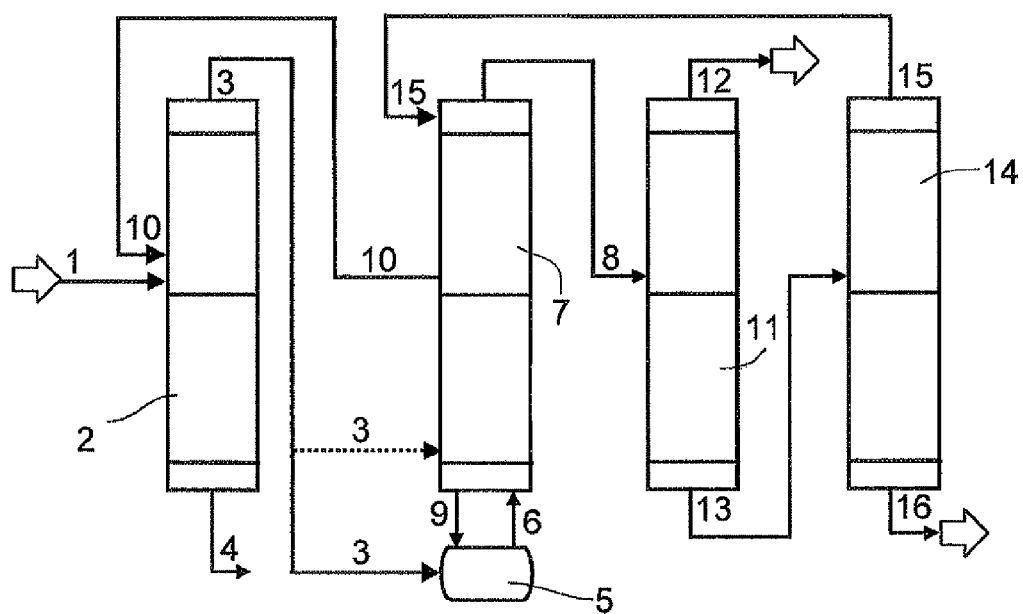

INTEGRATED METHOD FOR THE PREPARATION OF TRIOXANE FROM FORMALDEHYDE

RELATED APPLICATIONS

This application is a national stage application (under 35 U.S.C. §371) of PCT/EP2007/055694, filed Jun. 11, 2007, which claims benefit of European Application No. 06115287.2, filed Jun. 12, 2006.

The invention relates to an integrated process for preparing trioxane from formaldehyde.

Trioxane is generally prepared by reactive distillation of aqueous formaldehyde solution in the presence of acidic catalysts. This affords a mixture comprising trioxane, formaldehyde and water as distillate. The trioxane is subsequently extracted from this mixture by extraction with halogenated hydrocarbons such as methylene chloride or 1,2-dichloroethane, or other water-immiscible solvents.

DE-A 1 668 867 describes a process for removing trioxane from mixtures comprising water, formaldehyde and trioxane by extraction with an organic solvent. In this process, an extraction zone consisting of two subzones is charged at one end with an organic, virtually water-immiscible extractant for trioxane, and at the other end with water. Between the two subzones, the distillate from the trioxane synthesis to be separated is fed. On the side of the solvent feed, an aqueous formaldehyde solution is then obtained, and, on the side of the water feed, a virtually formaldehyde-free solution of trioxane in the organic solvent.

A disadvantage of this procedure is the occurrence of extractant which has to be purified. Some of the extractants used are hazardous substances (T or T+substances in the context of the German Hazardous Substances Regulations), whose handling entails special precautions.

DE-A 197 32 291 describes a process for removing trioxane from an aqueous mixture which consists substantially of trioxane, water and formaldehyde, by removing trioxane from the mixture by pervaporation and separating the trioxane-enriched permeate by rectification into pure trioxane on the one hand and an azeotropic mixture of trioxane, water and formaldehyde on the other. In one example, an aqueous mixture consisting of 40% by weight of trioxane, 40% by weight of water and 20% by weight of formaldehyde is separated in a first distillation column under standard pressure into a water/formaldehyde mixture and into an azeotropic trioxane/water/formaldehyde mixture. The azeotropic mixture is passed into a pervaporation unit which comprises a membrane composed of polydimethylsiloxane with a hydrophobic zeolite. The trioxane-enriched mixture is separated in a second distillation column under standard pressure into trioxane and, in turn, into an azeotropic mixture of trioxane, water and formaldehyde. This azeotropic mixture is recycled upstream of the pervaporation stage.

This procedure is very costly and inconvenient. The pervaporation unit in particular entails high capital costs.

It is an object of the invention to provide an alternative process for preparing trioxane from aqueous formaldehyde solution to obtain pure trioxane. It is a particular object to provide a process which avoids the performance of extraction steps or pervaporation steps for obtaining pure trioxane.

The object is achieved by an integrated process for preparing trioxane from formaldehyde, comprising the steps of:
a) feeding a feed stream A1 comprising formaldehyde and water and a recycle stream B3 comprising predominantly water and additionally formaldehyde and trioxane to a formaldehyde concentration unit and separating it into a formaldehyde-rich stream A2 and a stream A3 consisting essentially of water;
b) feeding a product stream C1 comprising trioxane and water, a recycle stream E1 comprising trioxane and water, and, if appropriate, the formaldehyde-rich stream A2 to a first low-pressure distillation column and distilling at a pressure of from 0.1 to 1.5 bar, and withdrawing a trioxane-enriched stream B1 comprising predominantly trioxane and additionally water and formaldehyde, a bottom draw stream B2 consisting essentially of formaldehyde and water, and the recycle stream B3 comprising predominantly water and additionally formaldehyde and trioxane as a side draw stream;
c) feeding the bottom draw stream B2 and, if appropriate, the stream A2 to a trioxane synthesis reactor and allowing them to react to obtain the stream C1 comprising trioxane, water and formaldehyde;
d) feeding the stream B1 to a medium-pressure distillation column and distilling at a pressure of from 1.0 to 4.0 bar to obtain a low boiler stream D1 comprising methanol, methylal and methyl formate, and a stream D2 comprising predominantly trioxane and additionally formaldehyde and water;
e) feeding the stream D2 to a high-pressure distillation column and distilling at a pressure of from 2.0 to 10.0 bar to obtain the recycle stream E1 comprising trioxane and water, and a product stream E2 consisting essentially of trioxane; the stream A2 being fed either to the low-pressure distillation column or to the trioxane synthesis reactor or to both.

"Consisting essentially of" is intended hereinbefore and hereinafter to mean that the stream in question consists of at least 80% by weight, preferably of at least 90% by weight, of the components mentioned. "Predominantly comprising" is intended to mean that the component mentioned constitutes the main component in the stream, and is preferably present therein to an extent of at least 50% by weight.

Trioxane, formaldehyde and water are known to form a ternary azeotrope which, at a pressure of 1 bar, consists of 69% by weight of trioxane, 5% by weight of formaldehyde and 26% by weight of water.

According to the invention, the ternary azeotrope is separated by a pressure swing distillation, by carrying out a first and a second distillation stage at different pressures. In a low-pressure distillation stage, a trioxane-rich trioxane/water/formaldehyde mixture which comprises only a little formaldehyde is removed from a trioxane- and formaldehyde-rich aqueous mixture. The trioxane-rich trioxane/water/formaldehyde mixture is separated in a downstream high-pressure distillation stage into a trioxane-rich trioxane/water/formaldehyde mixture on the one hand and virtually pure trioxane on the other hand. Between the low-pressure distillation stage and the high-pressure distillation stage, a medium-pressure distillation stage is also provided to remove low boilers. According to the invention, a formaldehyde/water mixture with a high water content is also withdrawn as a side draw from the low-pressure distillation stage, and is fed to a formaldehyde concentration stage together with the aqueous formaldehyde feed stream for water removal.

Useful high-pressure, medium-pressure and low-pressure distillation columns include any distillation columns, such as columns with random packing or structured packing. The distillation columns may comprise any internals, structured packings or random packings. Hereinafter, all pressure data relate to the pressure at the top of the column in question.

In a first process step a), a feed stream A1 comprising formaldehyde and water and a recycle stream B3 comprising predominantly water and additionally formaldehyde and trioxane are fed to a formaldehyde concentration unit and separated into a formaldehyde-containing stream A2 and a stream A3 consisting essentially of water.

In general, the feed stream A1 comprises from 20 to 65% by weight of formaldehyde and from 35 to 80% by weight of water. The recycle stream B3 comprises generally from 15 to 70% by weight of water, from 10 to 50% by weight of formaldehyde and from 1 to 30% by weight of trioxane. The formaldehyde-rich stream A2 comprises generally from 45 to 75% by weight of formaldehyde, from 20 to 55% by weight of water and from 0.1 to 15% by weight of trioxane. The stream A3 consisting essentially of water comprises generally from 90 to 100% by weight of water and additionally also small amounts of formaldehyde and formic acid and other components typically formed in the trioxane synthesis, for example dimethoxydimethyl ether and trimethoxydimethyl ether, for example in amounts of up to 10.0% by weight in total.

The concentration a) of the formaldehyde/water mixture is effected at a pressure of generally from 0.1 to 10.0 bar, preferably in a pressure distillation column at a pressure of generally from 1.0 to 10.0 bar, an aqueous stream which consists essentially of water being drawn off at the bottom of the column. Such a column can be operated, for example, at a pressure of 5.5 bar, a top temperature of 147° C. and a bottom temperature of 156° C.

In a process step b), a product stream C1 which comprises trioxane, water and formaldehyde and is obtained in a trioxane synthesis reactor, a recycle stream E1 comprising trioxane and water, and if appropriate the formaldehyde-rich stream A2 from the concentration unit are fed to a first low-pressure distillation column. The stream A2 may also be fed fully or partly directly to the trioxane synthesis reactor.

Preferably, stream E1 is fed to the low-pressure distillation column as a side feed in the upper third of the column, for example from 1 to 20 theoretical plates below the top of the column, and stream C1 as a side feed in the lower third of the column, preferably from 1 to 20 theoretical plates above the bottom of the column. When stream A2 is fed fully or partly to the low-pressure column, this is generally done in the lower third of the column, preferably from 1 to 15 theoretical plates above the bottom.

The low-pressure column is generally operated at a pressure of from 0.1 to 1.5 bar, preferably at a reduced pressure of from 0.5 to 0.9 bar. What is obtained is a trioxane-enriched stream B1 comprising predominantly trioxane and additionally water and formaldehyde, preferably as a top draw stream, a bottom draw stream B2 consisting essentially of formaldehyde and water, and the recycle stream B3 comprising predominantly water and additionally formaldehyde and trioxane as a side draw stream. The latter is generally withdrawn in the upper half, preferably in the upper third of the column. Optionally, a side draw stream B4 which comprises high boilers can be withdrawn from the low-pressure distillation column, preferably in the lower third, in order to discharge high boilers from the process.

The low-pressure distillation column has generally from 2 to 50, preferably from 4 to 40 theoretical plates.

The trioxane-enriched stream B1 comprises generally from 50 to 75% by weight of trioxane, from 1 to 25% by weight of formaldehyde and from 10 to 40% by weight of water. The bottom draw stream B2 comprises generally from 50 to 95% by weight of formaldehyde and from 5 to 40% by weight of water. In addition, it may comprise trioxane, generally in amounts of from 0 to 10% by weight, and also small amounts of formic acid if appropriate.

In a process step c), the bottom draw stream B2 and if appropriate stream A2 are fed to a trioxane synthesis reactor and allowed to react to obtain the stream C1 comprising trioxane and water. The stream A2 from the formaldehyde concentration can be fed fully or partly to the trioxane synthesis reactor.

In one embodiment of the process according to the invention, the water/formaldehyde mixture is converted in the trioxane synthesis stage c) in the presence of acidic homogeneous or heterogeneous catalysts such as ion exchange resins, zeolites, sulfuric acid or p-toluenesulfonic acid, at a temperature of generally from 70 to 130° C. The trioxane synthesis can be carried out in a fixed bed reactor or fluidized bed reactor over a heterogeneous catalyst, for example an ion exchange resin or zeolite.

The product stream C1 comprises generally trioxane, formaldehyde and water as main components and additionally the low boilers and high boilers typically formed in the trioxane synthesis. In general, it comprises from 0.1 to 35% by weight of trioxane. Low boilers and high boilers may be present, for example, in amounts of from 0.1 to 10.0% by weight.

The product stream C1 is preferably a vapor stream which is fed to the low-pressure distillation column close to the bottom. To discharge high boilers, a portion of the reaction mixture present in the trioxane synthesis reactor can be withdrawn from time to time.

In one embodiment of the process according to the invention, the trioxane synthesis stage c) and the low-pressure distillation stage b) are carried out together as a reactive distillation in one reaction column. In the stripping section, this may comprise a fixed catalyst bed of a heterogeneous catalyst. Alternatively, the reactive distillation can also be carried out in the presence of a homogeneous catalyst, in which case an acidic catalyst is present in the column bottom together with the water/formaldehyde mixture. The side draw stream B3 is then withdrawn from the reactive distillation column at a suitable point in the enriching section.

In a process step d), stream B1 is fed to a medium-pressure distillation column and distilled at a pressure of from 1.0 to 3.0 bar, preferably from 1.5 to 2.5 bar, to obtain a low boiler stream D1 which comprises generally methanol, methylal and methyl formate, and a stream D2 comprising predominantly trioxane and additionally formaldehyde and water. Stream D2 essentially has the same composition as stream B1, but essentially no longer comprises any low boilers.

In general, the low boiler stream consists of low boilers to an extent of at least 25% by weight, generally from methanol, methylal and methyl formate, and further low boilers if appropriate. The low boiler stream D1 is generally obtained as a top draw stream; stream D2 is withdrawn at the column bottom.

The medium-pressure distillation column has generally from 2 to 50, preferably from 4 to 40 theoretical plates.

In a further process step e), stream D2 is fed to a high-pressure distillation column and distilled at a pressure of from 2.0 to 10.0 bar, preferably from 3.0 to 6.0 bar, to obtain the recycle stream E1 comprising trioxane and water, and a product stream E2 consisting essentially of trioxane.

The recycle stream E1 comprises generally from 25 to 75% by weight of trioxane, from 10 to 50% by weight of water and from 1 to 25% by weight of formaldehyde. The trioxane stream E2 consists of trioxane generally to an extent of at least 99.0% by weight, preferably to an extent of at least 99.99% by weight. In addition, it may comprise water and formic acid, for example in amounts of >0.001% by weight, and high boilers.

The high-pressure distillation column has generally from 2 to 50, preferably from 4 to 40 theoretical plates.

Preferably, stream D2 is fed as a side feed to the high-pressure distillation column, stream E1 is withdrawn as a top draw stream and stream E2 is withdrawn as a bottom draw stream. Stream E2 can also be withdrawn as a gaseous side draw between feed and column bottom.

In a particularly preferred embodiment of the process according to the invention, the low-pressure distillation b) is carried out at a pressure of from 0.5 to 0.9 bar, the medium-pressure distillation c) at a pressure of from 1.5 to 2.5 bar, and the high-pressure distillation d) at a pressure of from 4.0 to 6.0 bar.

In one embodiment of the process according to the invention, the product stream E2 is purified even further. To this end, it can be fed to a purifying distillation column and distilled to obtain a pure trioxane stream F1 and a stream F2 comprising trioxane and high boilers. Stream F1 is generally withdrawn at the top of the column and may consist of pure trioxane having a purity of >99.9% by weight. Stream F2 is generally withdrawn at the bottom of the column and comprises high boilers. It additionally comprises trioxane, generally at least 10% by weight, preferably at least 50% by weight. Stream F2 is preferably recycled into the trioxane synthesis reactor. The trioxane purifying distillation column has generally from 1 to 40, preferably from 2 to 20 theoretical plates, and is generally operated at a pressure of from 0.1 to 2.5 bar, preferably from 0.75 to 1.5 bar.

Before it is fed into the purifying distillation column, stream E2 can be passed through an adsorption bed in order to remove traces of water and formic acid. Suitable adsorbents are, for example, molecular sieves, ion exchangers, zeolites, mordenites and silica gel, and also further adsorbents known to those skilled in the art.

The resulting pure trioxane, whose purity is generally >99.9% by weight, preferably >99.99% by weight, is preferably used to prepare polyoxymethylene (POM) or polyoxymethylene derivatives such as polyoxymethylene dimethyl ether (POMDME) and diaminodiphenylmethane (MDA).

The invention is illustrated in detail by the example which follows.

EXAMPLE

The FIGURE shows one embodiment of the process according to the invention. Only the main formaldehyde, water and trioxane components are shown. Streams whose content of these main components in total is less than 100% comprise the customary secondary components formed in the trioxane synthesis.

Feed stream 1 (=A1) composed of 49% by weight of formaldehyde and 51% by weight of water and recycle stream 10 (=B3) composed of 22% by weight of formaldehyde, 70% by weight of water and 8% by weight of trioxane are fed to the pressure distillation column 2. The pressure distillation column 2 is operated at a pressure of 6 bar, a bottom temperature of 160° C. and a top temperature of 148° C. The top draw stream 3 (=A2) obtained is a mixture of 54% by weight of formaldehyde, 41% by weight of water and 5% by weight of trioxane. The bottom draw stream 4 (=A3) obtained is a wastewater stream composed of 98% by weight of water which still comprises small amounts of formic acid (1.4% by weight) and formaldehyde (0.6% by weight). The top draw stream 3 is fed to the trioxane synthesis reactor 5 which is designed as a stirred vessel. Product stream 6 (=C1) comprises 25% by weight of trioxane, 22% by weight of water, 45% by weight of formaldehyde and 5% by weight of formic acid, and also small amounts of secondary components formed in the synthesis. This product stream 6 is fed in vaporous form to the low-pressure distillation column 7 having 20 theoretical plates at the level of the first theoretical plate. Also fed to distillation column 7 is a recycle stream 15 (=E1) composed of 65% by weight of trioxane, 31% by weight of water and 4% by weight of formaldehyde at the level of the 19th theoretical plate as a side feed. The column 7 is operated at a pressure of 0.6 bar; the bottom temperature is approx. 93° C., the top temperature approx. 62° C. A top draw stream 8 (=B1) composed of 3% by weight of formaldehyde, 26% by weight of water and 70% by weight of trioxane, and a bottom draw stream 9 (=B2) composed of 65% by weight of formaldehyde, 22% by weight of water and 7% by weight of trioxane are obtained. The latter is recycled into the trioxane synthesis reactor 5. Also withdrawn at the level of the 14th theoretical plate is the recycle stream 10 (=B3) as a side draw stream. The top draw stream 8 is fed to the medium-pressure distillation column 11 having 23 theoretical plates at the level of the 5th theoretical plate. The column 11 is operated at a pressure of 1.6 bar; the bottom temperature is approx. 105° C., the top temperature approx. 62° C. The top draw stream 12 (=D1) obtained is a mixture of 19% by weight of methanol, 54% by weight of methylal and 25% by weight of methyl formate. The bottom draw stream 13 (=D2) obtained is a mixture of 3% by weight of formaldehyde, 26% by weight of water and 71% by weight of trioxane. The bottom draw stream 13 is fed to the high-pressure distillation column 14 having 24 theoretical plates at the level of the 22nd theoretical plate. This column is operated at 5 bar; the bottom temperature is approx. 176° C., the top temperature approx. 143° C. The recycle stream 15 (=E1) is obtained as the top draw stream and a pure product stream 16 (=E2) composed of >99.9% by weight of trioxane as the bottom draw stream.

What is claimed is:
1. An integrated process for preparing trioxane from formaldehyde, comprising:
   a) feeding a feed stream A1 comprising formaldehyde and water and a recycle stream B3 comprising water as the main component and additionally formaldehyde and trioxane to a formaldehyde concentration unit and separating it into a formaldehyde-rich stream A2 and a stream A3 comprising at least 80% by weight of water;
   b) feeding a product stream C1 comprising trioxane, water and formaldehyde, a recycle stream E1 comprising trioxane, water, and formaldehyde, and optionally said stream A2 to a first low-pressure distillation column and distilling at a pressure of from 0.1 to 1.5 bar, and withdrawing a trioxane-enriched stream B1 comprising trioxane as a main component and additionally water and formaldehyde, a bottom draw stream B2 comprising at least 80% by weight of formaldehyde and water, and said recycle stream B3 as a side draw stream;
   c) feeding said bottom draw stream B2 and optionally said stream A2 to a trioxane synthesis reactor and reacting said streams to obtain said product stream C1;
   d) feeding said stream B1 to a medium-pressure distillation column and distilling at a pressure of from 1.0 to 3.0 bar to obtain a low boiler stream D1 comprising methanol, methylol, and methyl formate, and a stream D2 comprising predominantly trioxane and additionally formaldehyde and water;

e) feeding said stream D2 to a high-pressure distillation column and distilling at a pressure of from 2.5 to 10.0 bar to obtain said recycle stream E1 and a product stream E2 comprising at least 80% by weight of trioxane;

wherein said stream A2 is fed either to said low-pressure distillation column or said trioxane synthesis reactor or both.

2. The process of claim 1, wherein said low-pressure distillation of b) is carried out at a pressure of from 0.1 to 1.5 bar, said medium-pressure distillation of c) is carried out at a pressure of from 1.0 to 4.0 bar, and said high-pressure distillation of d) is carried out at a pressure of from 2.0 to 10.0 bar.

3. The process of claim 1, wherein said stream B1 is withdrawn from said low-pressure distillation column as a top draw stream.

4. The process of claim 1, wherein stream E1 is fed to said low-pressure distillation column as a side feed in the upper third of the column, from 1 to 20 theoretical plates below the top, and stream C1 is fed to said low-pressure distillation as a side feed in the lower third of the column, from 1 to 20 theoretical plates above the bottom.

5. The process of claim 1, wherein stream D1 is withdrawn from said medium-pressure distillation column as a top draw stream and stream D2 is withdrawn from said medium-pressure distillation column as a bottom draw stream.

6. The process of claim 1, wherein stream E1 is withdrawn from said high-pressure distillation column as a top draw stream and stream E2 is withdrawn from said high-pressure distillation column as a bottom draw stream.

7. The process of claim 1, wherein said formaldehyde concentration unit in a) is a pressure distillation column and stream A3 is withdrawn as an aqueous bottom draw stream.

8. The process of claim 1, wherein said formaldehyde concentration unit is a falling-film evaporator.

9. The process of claim 1, further comprising withdrawing a side draw stream B4 comprising high boilers from said low-pressure distillation column in the lower third, from 1 to 5 theoretical plates above the bottom.

10. The process of claim 1, further comprising withdrawing a stream B4 comprising high boilers from said trioxane synthesis reactor.

11. The process of claim 1, further comprising feeding said product stream E2 to a purifying distillation column and distilling it to obtain a pure trioxane stream F1 and a stream F2 comprising trioxane and high boilers.

12. The process of claim 11, wherein said stream F2 is recycled into said trioxane synthesis reactor.

13. The process of claim 11, wherein said stream E2 is passed through an adsorption bed for removal of traces of water and formic acid prior to feeding it into said purifying distillation column.

* * * * *